United States Patent
Liou et al.

(10) Patent No.: US 9,446,085 B2
(45) Date of Patent: Sep. 20, 2016

(54) HERBAL EXTRACT AND METHOD OF INHIBITING FAT-STORAGE FUNCTION OF ADIPOCYTES

(71) Applicant: HAN SHENG BIOTECH CO., LTD., Pingtung County (TW)

(72) Inventors: Shorong-Shii Liou, Pingtung County (TW); I-Min Liu, Pingtung County (TW); Chia-Ju Chang, Pingtung County (TW)

(73) Assignee: HAN SHENG BIOTECH CO., LTD, Changjhih Townshhip, Pingtung County (TW)

( * ) Notice: Subject to any disclaimer, the term of this patent is extended or adjusted under 35 U.S.C. 154(b) by 64 days.

(21) Appl. No.: 14/162,101

(22) Filed: Jan. 23, 2014

(65) Prior Publication Data

US 2015/0202242 A1    Jul. 23, 2015

(51) Int. Cl.
*A61K 36/8994* (2006.01)
*A61K 36/254* (2006.01)
*A61K 36/9068* (2006.01)

(52) U.S. Cl.
CPC ......... *A61K 36/254* (2013.01); *A61K 36/8994* (2013.01); *A61K 36/9068* (2013.01); *A61K 2236/00* (2013.01)

(58) Field of Classification Search
None
See application file for complete search history.

(56) References Cited

U.S. PATENT DOCUMENTS

| 8,168,237 B2 | 5/2012 | Seo et al. |
| 8,247,001 B2 | 8/2012 | Huang et al. |
| 8,501,249 B2 * | 8/2013 | Liu et al. ............. 424/756 |
| 8,524,291 B2 | 9/2013 | Huang et al. |

FOREIGN PATENT DOCUMENTS

| JP | 08073369 A | * | 3/1996 |
| KR | 2002077581 A | * | 10/2002 |

OTHER PUBLICATIONS 2015 https://en.wikipedia.org/wiki/Job%27s_Tear.*

* cited by examiner

*Primary Examiner* — Terry A McKelvey
*Assistant Examiner* — Catheryne Chen
(74) *Attorney, Agent, or Firm* — Muncy, Geissler, Olds & Lowe, P.C.

(57) ABSTRACT

The present invention discloses an herbal extract of inhibiting fat-storage function of adipocytes. The herbal extract comprises an *Acanthopanax senticosus* extract, a *Zingiber officinale* Roscoe extract and a *Coix lachryma-jobi* L. extract, wherein a weight percentage of the *Acanthopanax senticosus* extract is 60 to 80% by weight of the herbal extract, wherein a weight percentage of the *Zingiber officinale* Roscoe extract is 10 to 30% by weight of the herbal extract, wherein a weight percentage of the *Coix lachryma-jobi* L. extract is 10% by weight of the herbal extract.

5 Claims, 18 Drawing Sheets

HERBAL EXTRACT AND METHOD OF INHIBITING FAT-STORAGE FUNCTION OF ADIPOCYTES

BACKGROUND OF THE INVENTION

1. Field of the Invention

The present invention generally relates to an herbal extract and, more particularly, to an herbal extract with property of inhibiting fat-storage function of adipocytes. The present invention further relates to a method of inhibiting fat-storage function of adipocytes thereof.

2. Description of the Related Art

Obesity is a medical condition in which excess body fat accumulates to the extent that it may have an adverse effect on health leading to reduced lifespan and/or increased health problems. Obesity increases the likelihood of various diseases, particularly heart disease and type II diabetes. Therefore, the way against obesity is also the way preventing from the obesity-derived diseases or conditions.

Adipocytes are generally divided into two types of cells, white fat cells and brown fat cells. The white fat cells play a key role in energy balance. Excess energy transforms to triglycerides and stores in white fat cells. On the other hand, triglycerides are decomposed and transformed to fatty acids and glycerin when lacking of energy. Therefore, from point of view of energy balance, obesity indicates the imbalance between energy emergence and consumption. Excess energy stores in the white fat cells in the form of triglycerides, thereby resulting in hypertrophy of the white fat cells.

Conventional anti-obesity medicine includes sibutramine, also known as meridian, and orlistat, also known as xenical. Meridian prolongs the time effect of norepinephrine and serotonin, accelerates the metabolism of organism and finally to advance the consumption of fat. Xenical inactivates lipase in small intestine, to inhibit the lipolytic effects of small intestine, as well as the absorption of fatty acid whereof.

However, the conventional anti-obesity medicine usually accompanies with plenty of side effects, such as thirsty, insomnia, heat ache and constipation, which may result in various inconvenience to people. In light of this, it is necessary to provide an anti-obesity medicine, which is natural, effective and less risky, for the sake of providing a new strategy for losing weight in an easy and convenient process without any side effects.

SUMMARY OF THE INVENTION

It is therefore the objective of this invention to provide an herbal extract of inhibiting fat-storage function of adipocytes, preventing from obesity-derived diseases or conditions.

It is another objective of this invention to provide a method of inhibiting fat-storage function of adipocytes, preventing from side effects induced by the conventional medicine.

One embodiment of the invention discloses an herbal extract comprising: an *Acanthopanax senticosus* extract, a *Zingiber officinale* Roscoe extract and a *Coix lachryma-jobi* L. extract, wherein a weight percentage of the *Acanthopanax senticosus* extract is 60 to 80% by weight of the herbal extract, wherein a weight percentage of the *Zingiber officinale* Roscoe extract is 10 to 30% by weight of the herbal extract, wherein a weight percentage of the *Coix lachryma-jobi* L. extract is 10% by weight of the herbal extract. Preferably, the weight percentages of the *Acanthopanax senticosus* extract, the *Zingiber officinale* Roscoe extract, and the *Coix lachryma-jobi* L. extract are 80, 10, and 10% by weight of the herbal extract, respectively.

In a preferred form shown, the *Acanthopanax senticosus* extract is obtained by a process comprising: extracting an *Acanthopanax senticosus* sample with water in a weight-volumetric ratio of 1:1 to 1:10 at 45 to 55° C. to obtain an *Acanthopanax senticosus* liquid extract; and condensing the *Acanthopanax senticosus* liquid extract. Preferably, the process to obtain the *Acanthopanax senticosus* extract further comprises: before extracting the *Acanthopanax senticosus* sample with water, moistening the *Acanthopanax senticosus* sample with rice vinegar in a weight-volumetric ratio of 40:3, and then frying at 40 to 60° C. to obtain a vinegar-fried *Acanthopanax senticosus* sample, wherein the vinegar-fried *Acanthopanax senticosus* sample is extracted and condensed to obtain the *Acanthopanax senticosus* extract.

In a preferred form shown, the *Zingiber officinale* Roscoe extract is obtained by a process comprising: extracting a *Zingiber officinale* Roscoe sample with 95% ethanol in a weight-volumetric ratio of 1:1 to 1:10 at 45 to 55° C. to obtain a *Zingiber officinale* Roscoe liquid extract; and condensing the *Zingiber officinale* Roscoe liquid extract. Preferably, the process to obtain the *Zingiber officinale* Roscoe extract further comprises: before extracting the *Zingiber officinale* Roscoe sample with 95% ethanol, drying the *Zingiber officinale* Roscoe sample till water content of the *Zingiber officinale* Roscoe sample is lower than 10%, and then frying at 80 to 120° C. to obtain a fried *Zingiber officinale* Roscoe sample, wherein the fried *Zingiber officinale* Roscoe sample is extracted and condensed to obtain the *Zingiber officinale* Roscoe extract.

In a preferred form shown, the *Coix lachryma-jobi* L. extract is obtained by a process comprising: extracting an *Coix lachryma-jobi* L. sample with 95% ethanol in a weight-volumetric ratio of 1:1 to 1:10 at 45 to 55° C. to obtain an *Coix lachryma-jobi* L. liquid extract; and condensing the *Coix lachryma-jobi* L. liquid extract. Preferably, the process to obtain the *Coix lachryma-jobi* L. extract further comprises: before extracting the *Coix lachryma-jobi* L. sample with water, frying the *Coix lachryma-jobi* L. sample at 40 to 60° C. to obtain a fried *Coix lachryma-jobi* L. sample, wherein the fried *Coix lachryma-jobi* L. sample is extracted and condensed to obtain the *Coix lachryma-jobi* L. extract.

In a preferred form shown, the extraction of the *Acanthopanax senticosus* sample, the *Zingiber officinale* Roscoe sample, and the *Coix lachryma-jobi* L. sample is performed for 8 hours.

The other embodiment of the invention discloses a method of inhibiting fat-storage function of adipocytes comprising: administering an effective amount of an herbal extract to a target in need thereof.

In another preferred form shown, the herbal extract is orally administered to the target in need in the effect amount of 100 to 600 mg/per kilogram of body weight per day for 12 weeks.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1A:
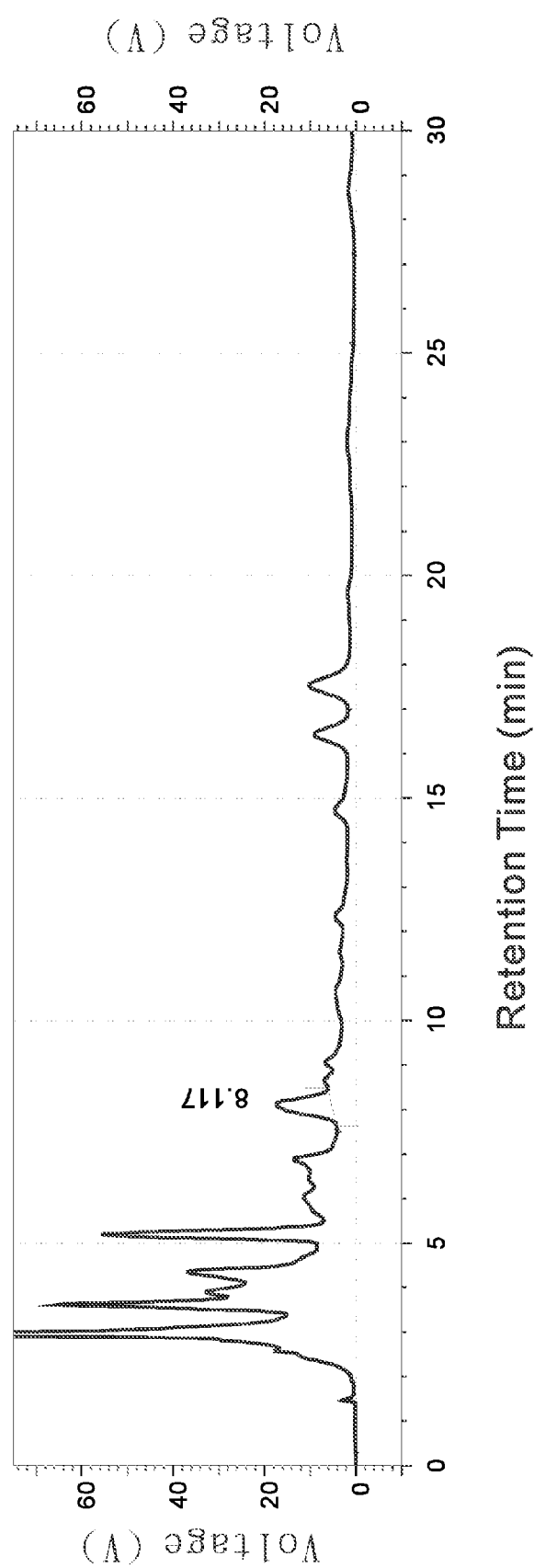
FIG. 1A depicts syringin content of group A1 using HPLC analysis.
Figure 1B:
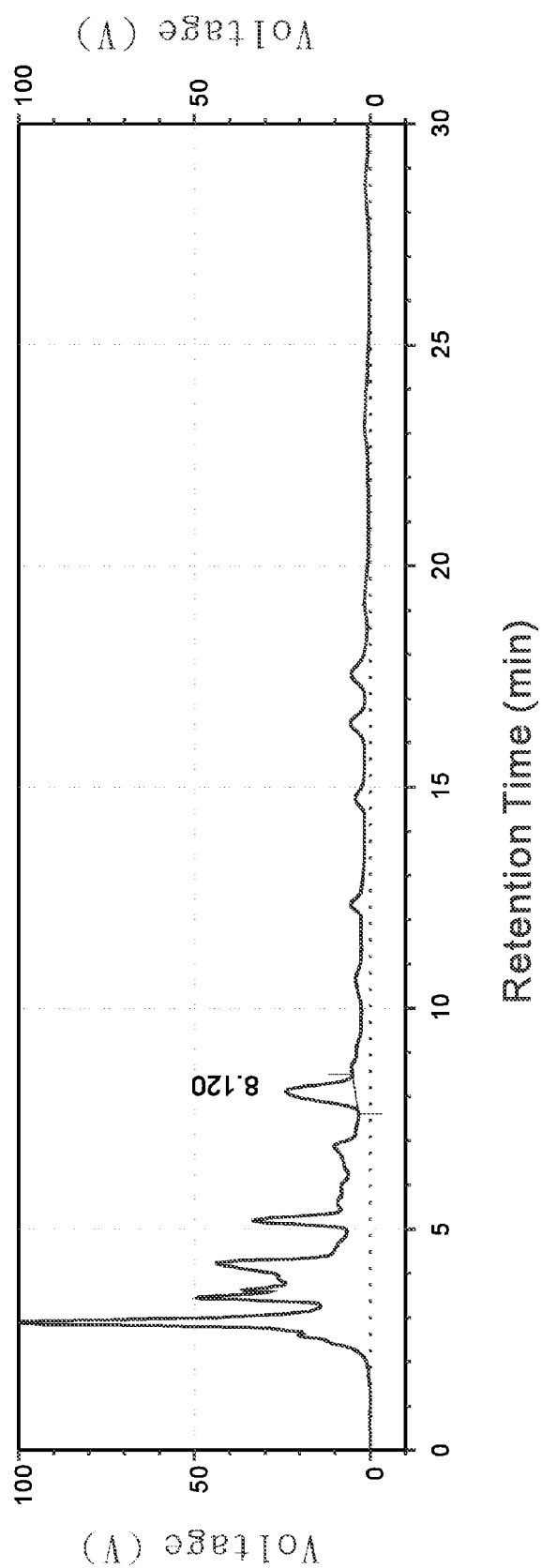
FIG. 1B depicts syringin content of group A2 using HPLC analysis.
Figure 1C:
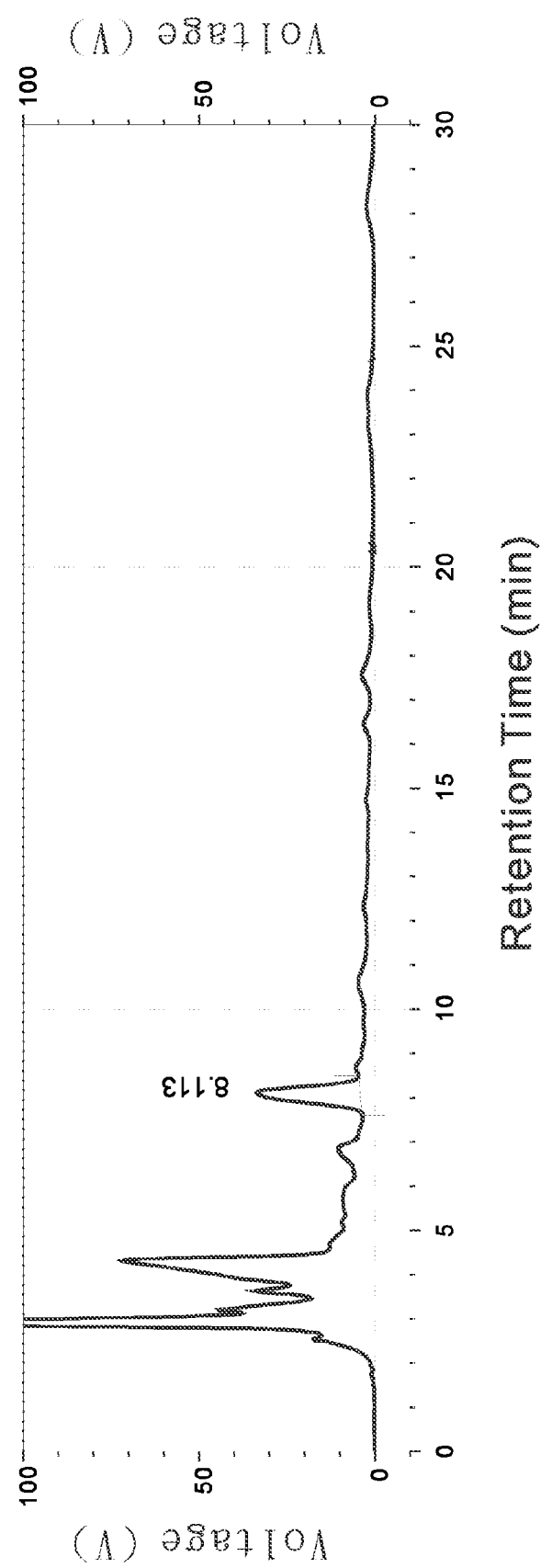
FIG. 1C depicts syringin content of group A3 using HPLC analysis.
Figure 1D:
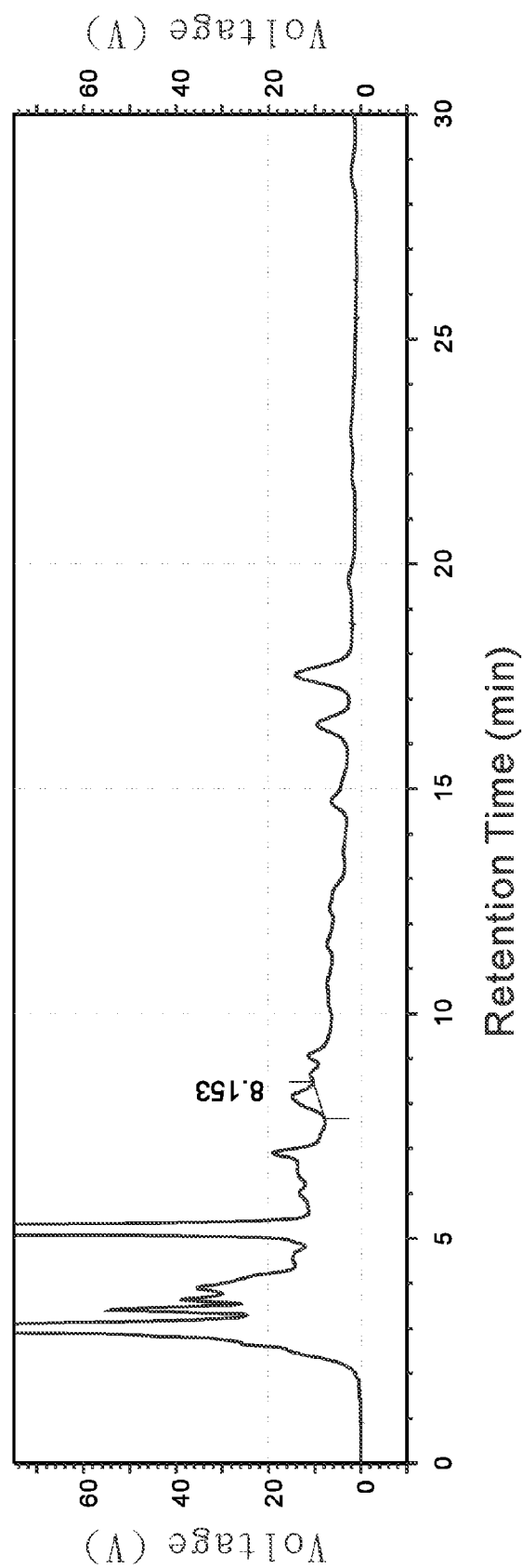
FIG. 1D depicts syringin content of group A4 using HPLC analysis.
Figure 1E:
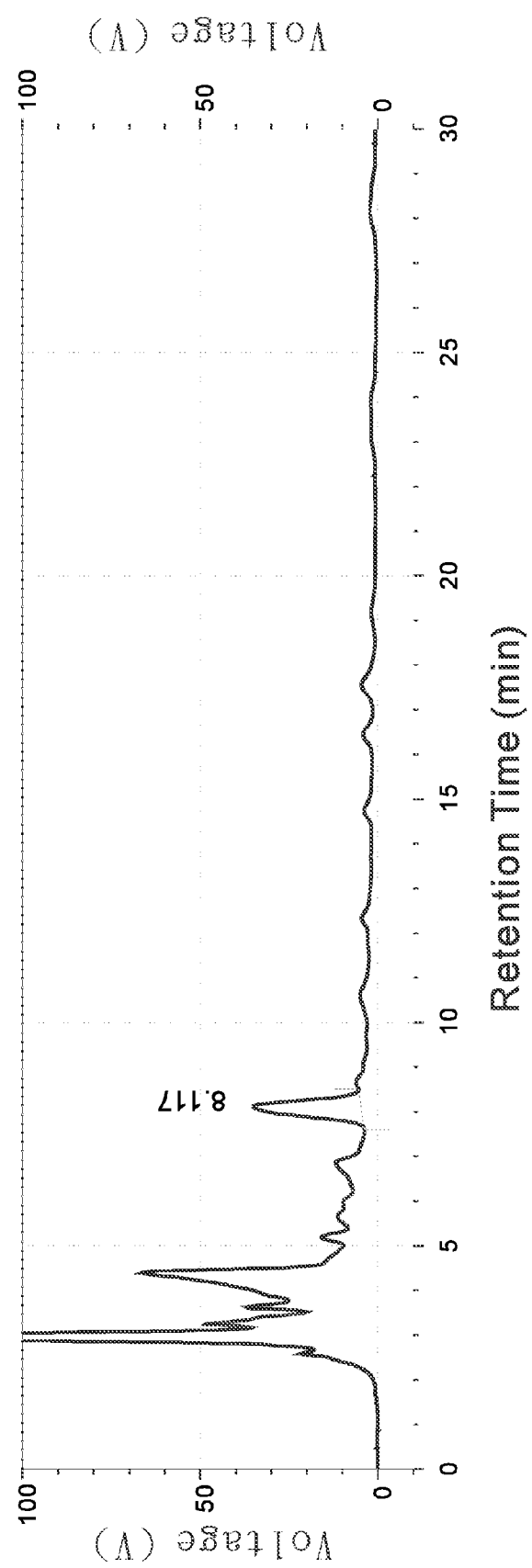
FIG. 1E depicts syringin content of group A5 using HPLC analysis.
Figure 1F:
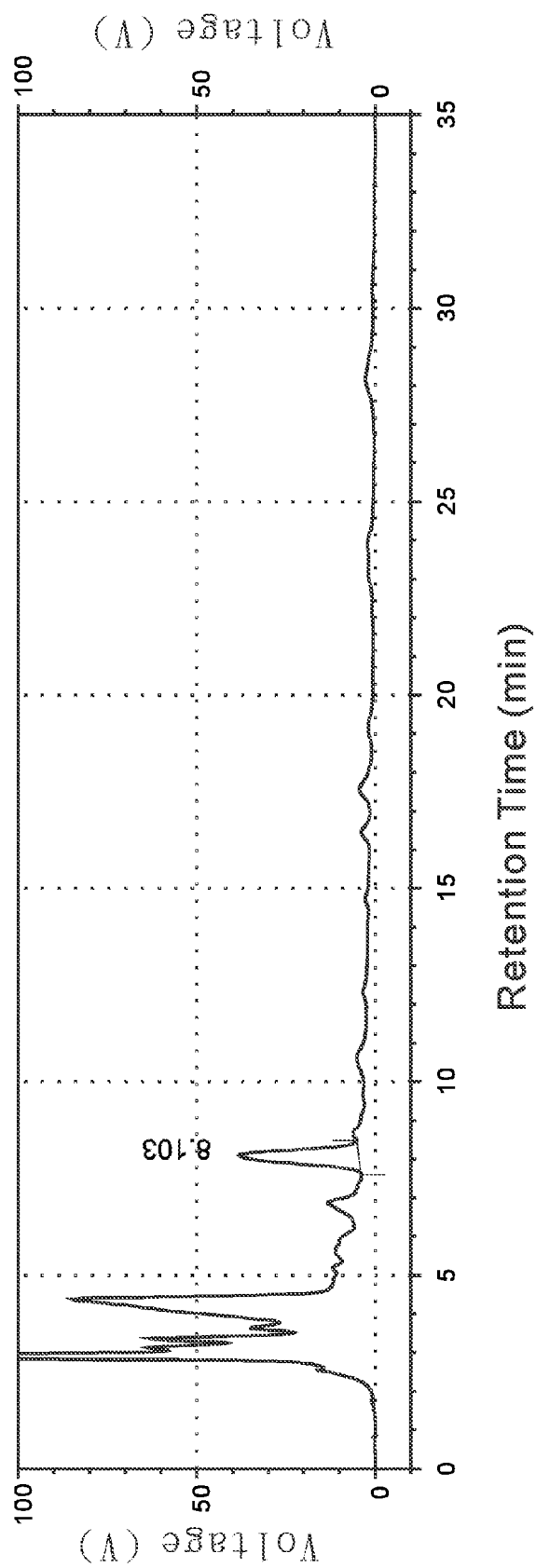
FIG. 1F depicts syringin content of group A6 using HPLC analysis.
Figure 2A:
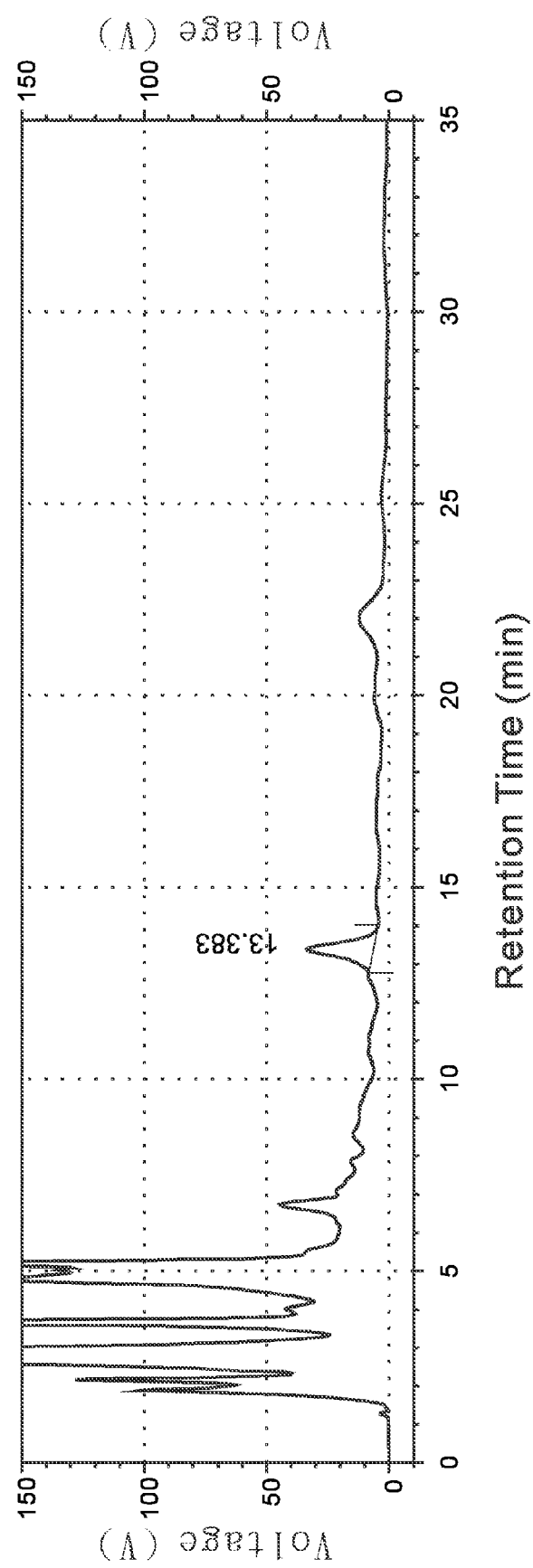
FIG. 2A depicts elentheroside content of group A1 using HPLC analysis.
Figure 2B:
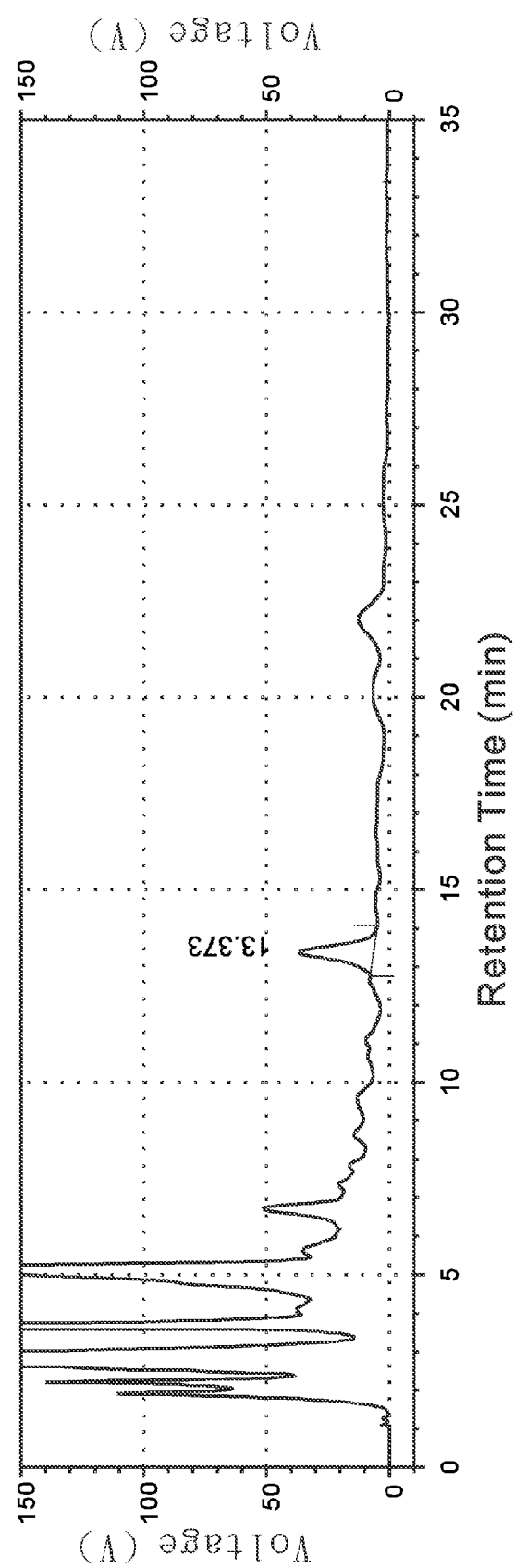
FIG. 2B depicts elentheroside content of group A2 using HPLC analysis.
Figure 2C:
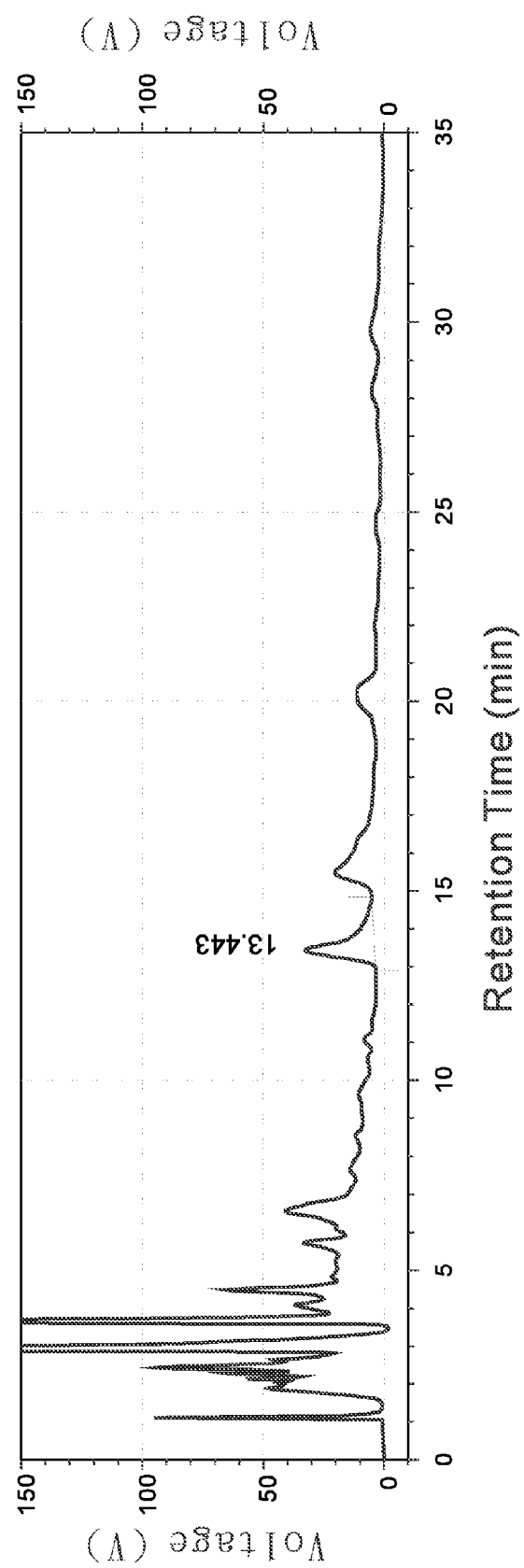
FIG. 2C depicts elentheroside content of group A3 using HPLC analysis.
Figure 2D:
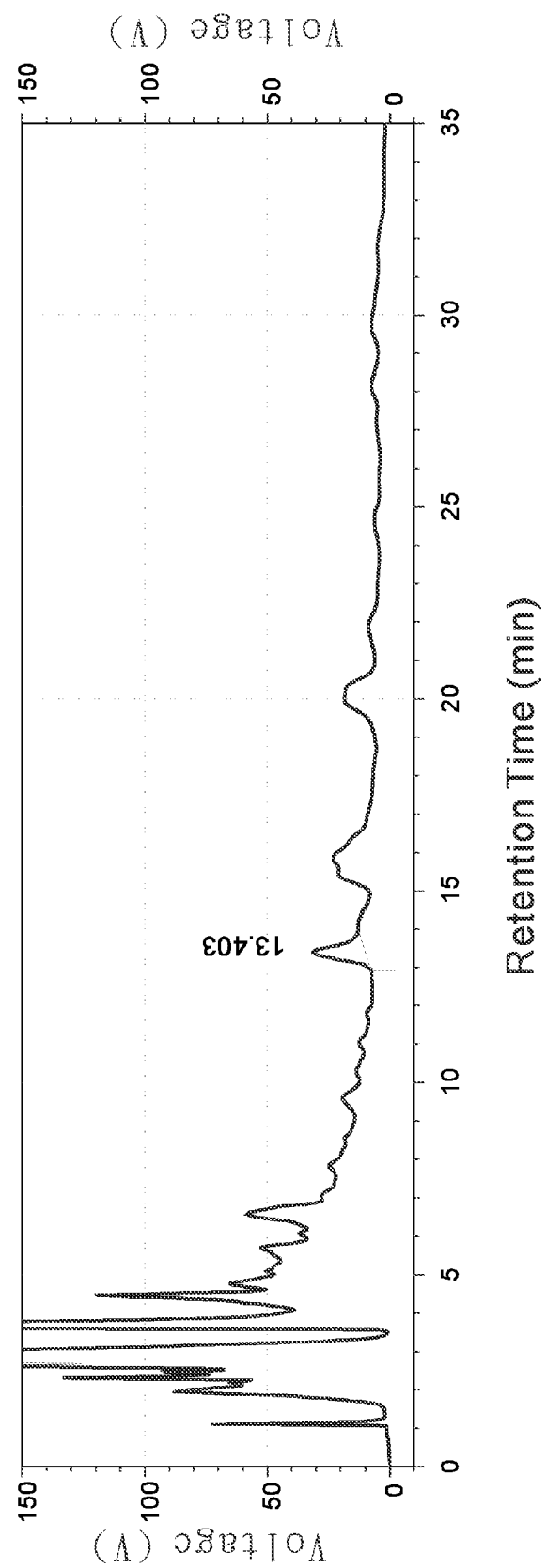
FIG. 2D depicts elentheroside content of group A4 using HPLC analysis.
Figure 2E:
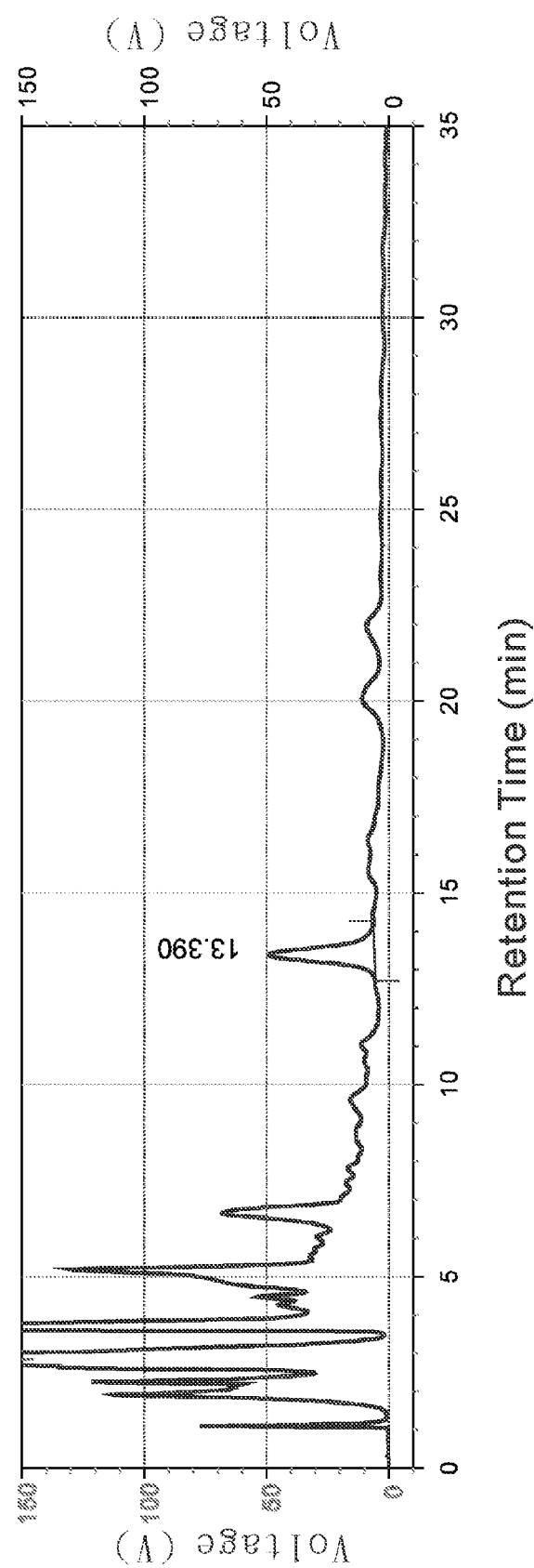
FIG. 2E depicts elentheroside content of group A5 using HPLC analysis.
Figure 2F:
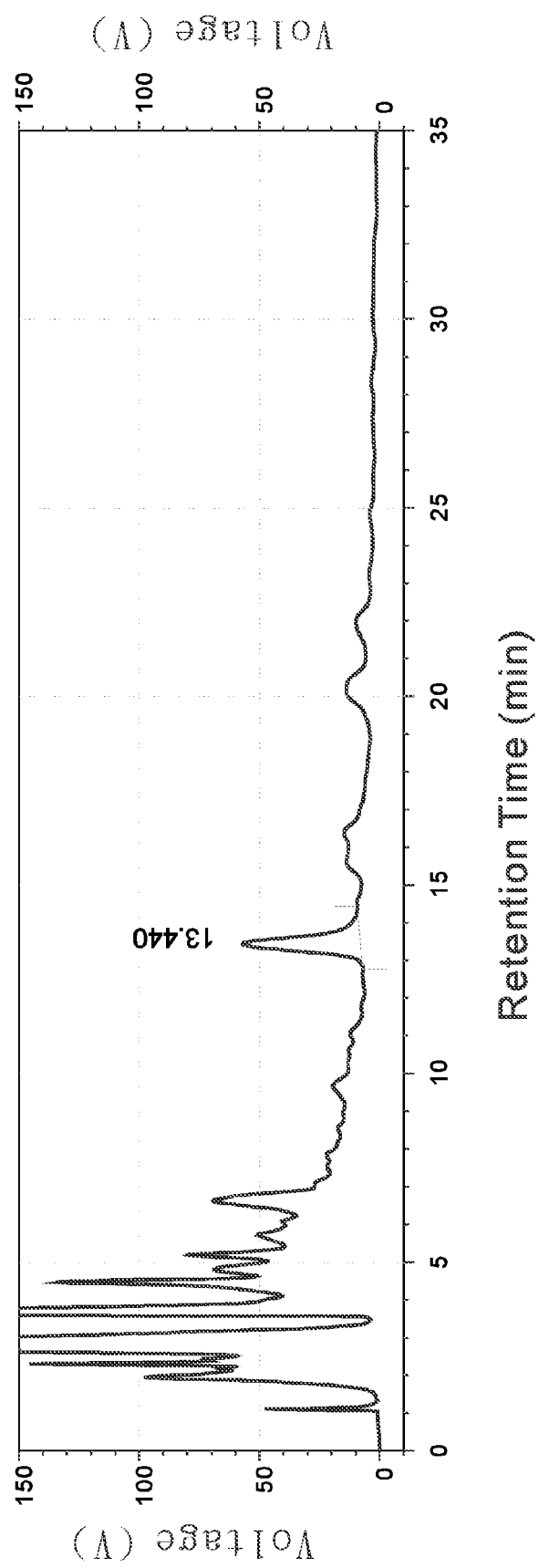
FIG. 2F depicts elentheroside content of group A6 using HPLC analysis.
Figure 3A:
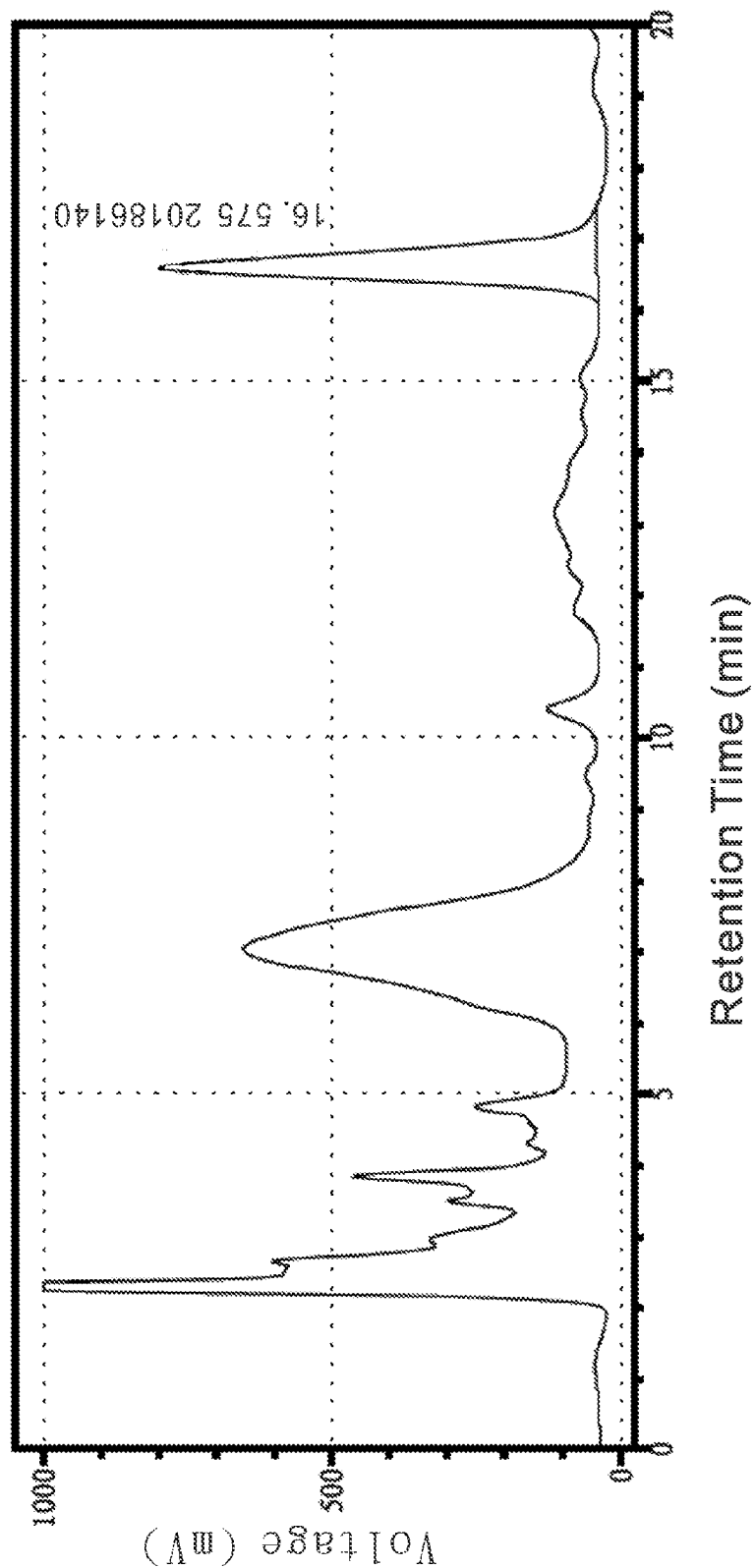
FIG. 3A depicts 6-gingerol content of group B1 using HPLC analysis.
Figure 3B:
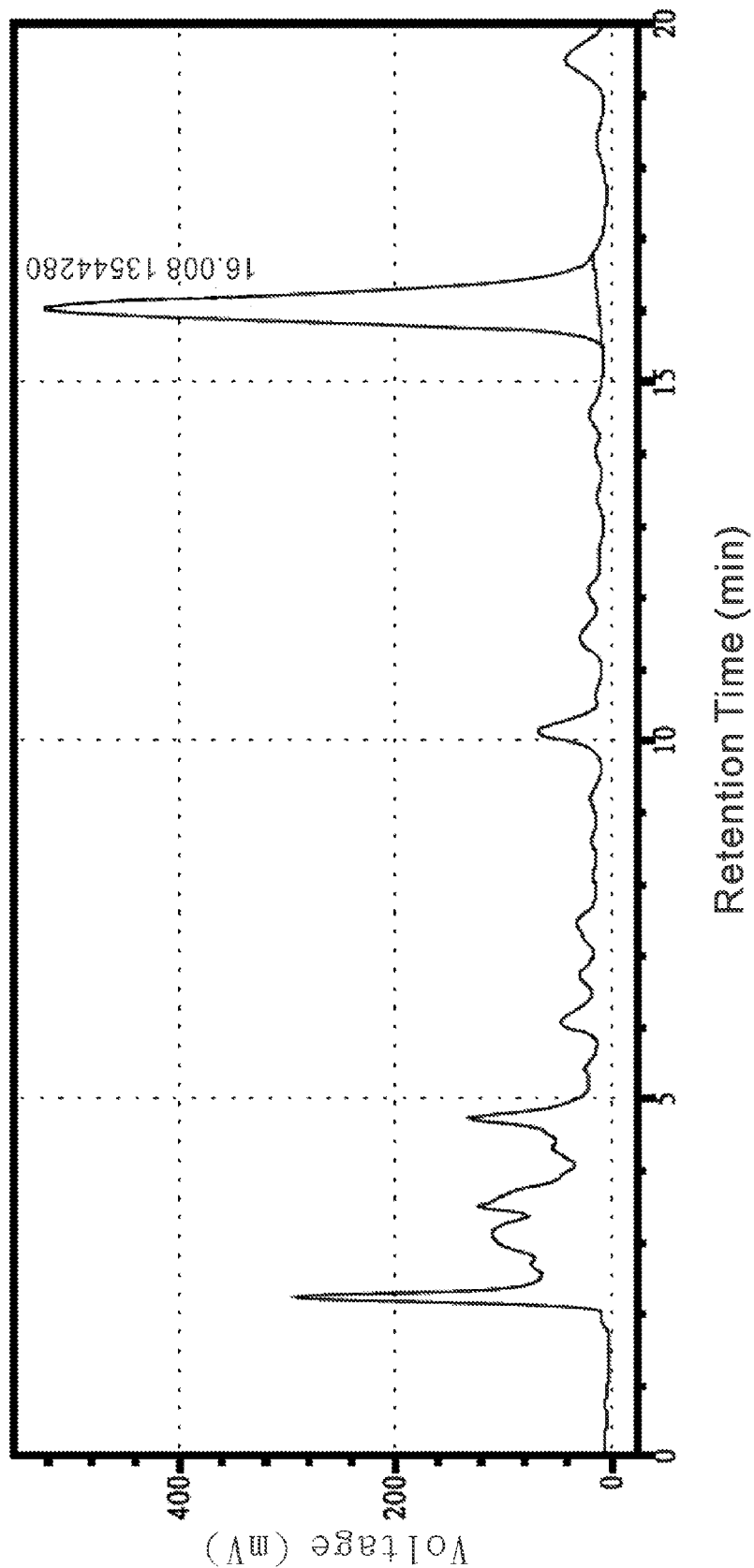
FIG. 3B depicts 6-gingerol content of group B2 using HPLC analysis.
Figure 3C:
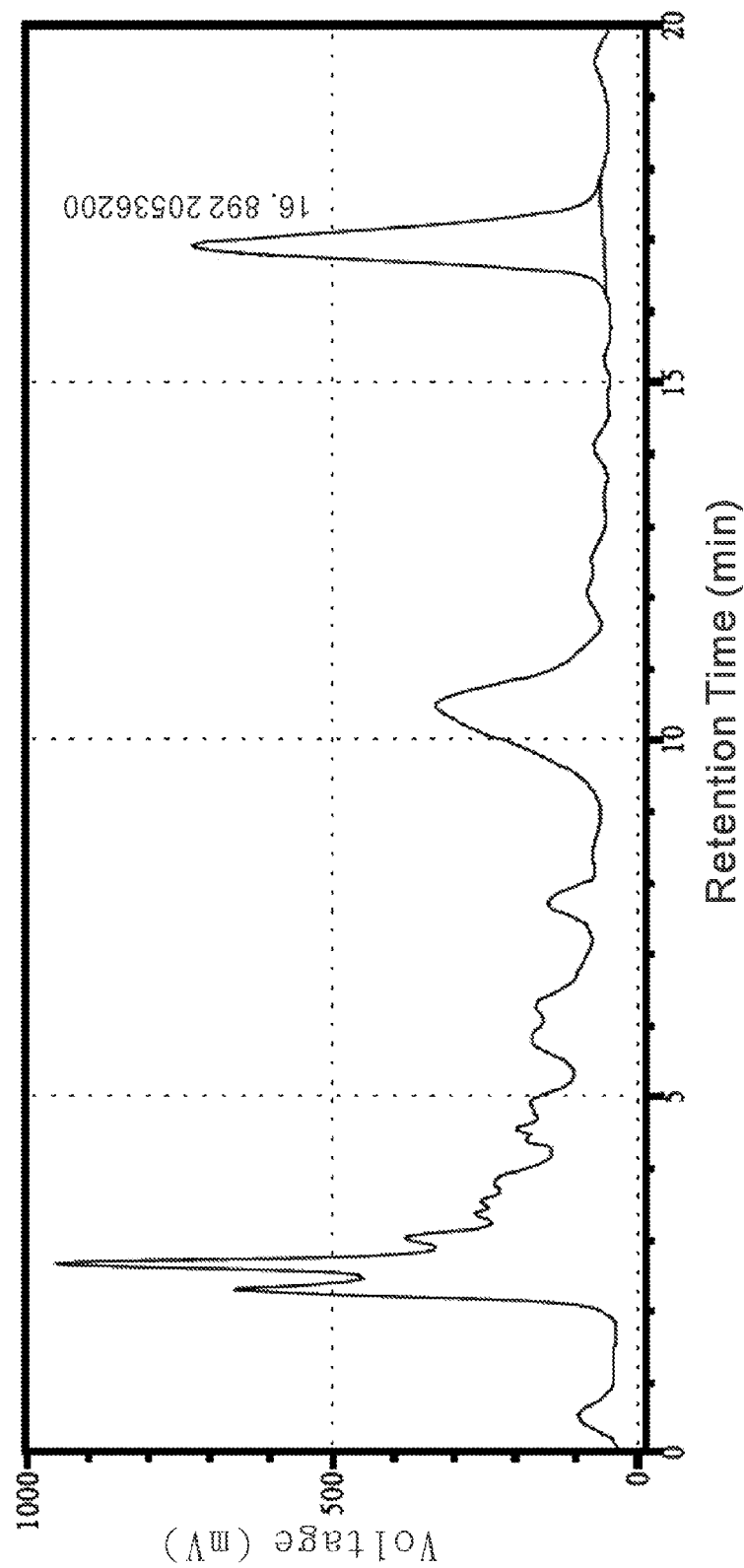
FIG. 3C depicts 6-gingerol content of group B3 using HPLC analysis.
Figure 3D:
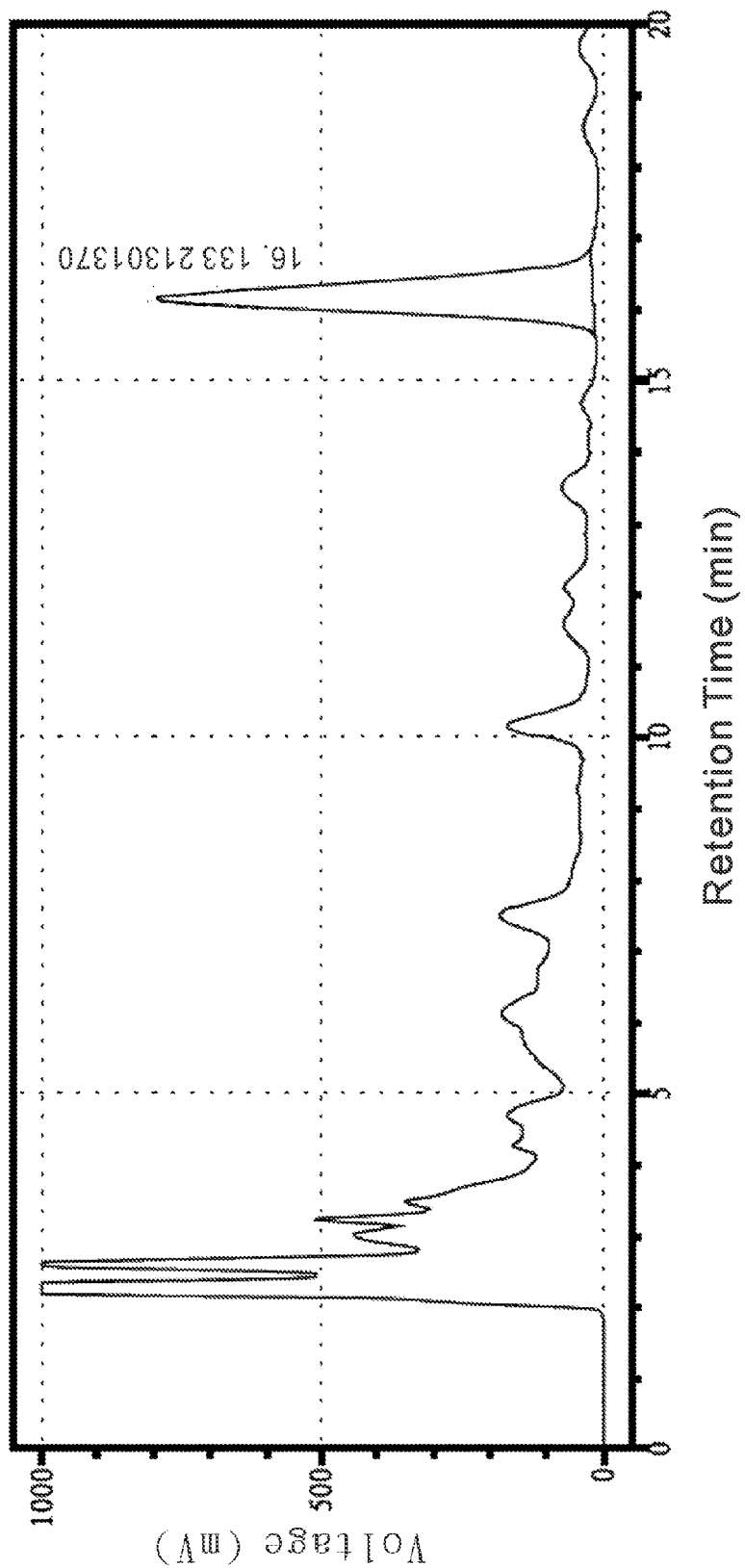
FIG. 3D depicts 6-gingerol content of group B4 using HPLC analysis.

In the various figures of the drawings, the same numerals designate the same or similar parts. Furthermore, when the terms "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

An herbal extract according to preferred teachings of the invention comprises: 60 to 80 wt % of an *Acanthopanax senticosus* extract, 10 to 30 wt % of a *Zingiber officinale* Roscoe extract and 10 wt % of a *Coix lachryma-jobi* L. extract.

The *Acanthopanax senticosus* extract is extracted from an *Acanthopanax senticosus* sample, preferably selected from roots or stems of the *Acanthopanax senticosus* sample. The *Acanthopanax senticosus* extract contains syringin and elentheroside, with effects on anti-free radical, anti-oxidation, immunity, and anti-aging.

In a preferable embodiment, the *Acanthopanax senticosus* sample is from Taiwan or China, which has no pesticide residue and toxic heavy metal content under regulation. The *Acanthopanax senticosus* sample can be a raw sample without processing. Preferably, the *Acanthopanax senticosus* sample can be a processed sample with improved active ingredients contents. The processed sample can be obtained by moistening the raw sample with rice vinegar (acidity 4.5%) in a weight-volumetric ratio of 40:3, followed by frying at 40 to 60° C. to obtain a vinegar-fried sample. Alternatively, the processed sample can also be obtained by moistening the raw sample with rice vinegar (acidity 4.5%) in a weight-volumetric ratio of 40:3, followed by cooking at 110 to 150° C. for 4 hours to obtain a vinegar-cooked sample. Both the vinegar-fried sample and the vinegar-cooked sample have improved contents of active ingredients, syringin and elentheroside, than the raw sample.

In a preferable embodiment, the *Acanthopanax senticosus* extract is obtained, but not limited to, by a process comprising: extracting the raw sample or the processed sample with water in a weight-volumetric ratio of 1:1 to 1:10 at 45 to 55° C. for 8 hours with sonicated vibration (200 rpm) to obtain an liquid extract. A preferable weight-volumetric ratio of the raw sample or the processed sample with water is 1:2. The obtained liquid extract is further condensed to obtain the *Acanthopanax senticosus* extract.

The *Zingiber officinale* Roscoe extract is extracted from a *Zingiber officinale* Roscoe sample, preferably selected from roots or stems of the *Zingiber officinale* Roscoe sample. The *Zingiber officinale* Roscoe extract contains 6-gingerol, with effects on anti-free radical, anti-blood clotting, and anti-inflammation.

In a preferable embodiment, the *Zingiber officinale* Roscoe sample is from Taiwan or China, which has no pesticide residue and toxic heavy metal content under regulation. The *Zingiber officinale* Roscoe sample can be a raw sample without processing. Preferably, the *Zingiber officinale* Roscoe sample can be a processed sample with reduced spicy. The processed sample can be obtained by drying the raw sample till water content of the raw sample is lower than 10%, followed by frying at 80 to 120° C. to obtain a fried sample.

In a preferable embodiment, the *Zingiber officinale* Roscoe extract is obtained, but not limited to, by a process comprising: extracting the raw sample or the processed sample with 95% ethanol in a weight-volumetric ratio of 1:1 to 1:10 at 45 to 55° C. for 8 hours with sonicated vibration (200 rpm) to obtain an liquid extract. A preferable weight-volumetric ratio of the raw sample or the processed sample with 95% ethanol is 1:2. The obtained liquid extract is further condensed to obtain the *Zingiber officinale* Roscoe extract.

The *Coix lachryma-jobi* L. extract is extracted from a *Coix lachryma-jobi* L. sample, preferably selected from seeds of the *Coix lachryma-jobi* L. sample. The *Coix lachryma-jobi* L. extract contains coixol and coixenolide, with effects on blood lipid regulation.

In a preferable embodiment, the *Coix lachryma-jobi* L. sample is from Taiwan or China, which has no pesticide residue and toxic heavy metal content under regulation. The *Coix lachryma-jobi* L. sample can be a raw sample. Preferably, the *Coix lachryma-jobi* L. sample can be a processed sample with reduced cooling property, which is suitable for spleen-cold syndrome. The processed sample can be obtained by frying the raw sample at 40 to 60° C. to obtain a fried sample.

In a preferable embodiment, the *Coix lachryma-jobi* L. extract is obtained, but not limited to, by a process comprising: extracting the raw sample or the processed sample with 95% ethanol in a weight-volumetric ratio of 1:1 to 1:10 at 45 to 55° C. for 8 hours with sonicated vibration (200 rpm) to obtain an liquid extract. A preferable weight-volumetric ratio of the raw sample or the processed sample with water is 1:2. The obtained liquid extract is further condensed to obtain the *Coix lachryma-jobi* L. extract.

The process of extraction can be performed for several times. Thus active ingredients of the raw sample or the processed sample can effectively dissolve in solvents used in the process of extraction, water or 95% ethanol, which is a well-known means in the field.

The liquid extract can be performed by vacuum-concentration at 40 to 60° C. to remove 50 to 70% of total weight of the liquid extract. The resultant can be further frozen-dried at −40° C. to obtain the *Acanthopanax senticosus* extract, the *Zingiber officinale* Roscoe extract, and the *Coix lachryma-jobi* L. extract, respectively. The water content of the *Acanthopanax senticosus* extract, the *Zingiber officinale* Roscoe extract, and the *Coix lachryma-jobi* L. extract is under 7%.

The *Acanthopanax senticosus* extract, the *Zingiber officinale* Roscoe extract, and the *Coix lachryma-jobi* L. extract are then mixed to obtain the herbal extract of the invention. The herbal extract of the invention comprises 60 to 80 wt % of the *Acanthopanax senticosus* extract, 10 to 30 wt % of the *Zingiber officinale* Roscoe extract, and 10 wt % of the *Coix lachryma-jobi* L. extract. Preferably, the herbal extract of the invention comprises 80 wt % of the *Acanthopanax senticosus* extract, 10 wt % of the *Zingiber officinale* Roscoe extract, and 10 wt % of the *Coix lachryma-jobi* L. extract.

The herbal extract of the invention contains active ingredients such as syringin, elentheroside and 6-ginerol. By the ratio of the *Acanthopanax senticosus* extract, the *Zingiber officinale* Roscoe extract, and the *Coix lachryma-jobi* L. extract, the herbal extract of the invention shows effects on inhibiting fat-storage and anti-obesity.

Trial (A): Active Ingredients Contents of the *Acanthopanax senticosus* Extract

Raw, vinegar-cooked or vinegar-fried samples shown in TABLE 1 are used in the trial (A). 1 gram of the sample is extracted via sonicated vibration for 2 hours by 20 mL of methanol. The resultant is filtrated by a No. 3 filter paper, followed by vacuum-concentration at 35° C. until the total volume is 5 mL.

TABLE 1

| Groups | Samples | | Syringin | Elentheroside |
| | Origin | Processing | content (mg/g) | content (mg/g) |
| --- | --- | --- | --- | --- |
| A1 | Taiwan | Raw | 2.27 ± 0.81 | 0.77 ± 0.28 |
| A2 | Taiwan | Vinegar-cooked | 2.96 ± 0.72 | 1.61 ± 0.32 |
| A3 | Taiwan | Vinegar-fried | 3.46 ± 0.21 | 2.31 ± 0.26 |
| A4 | China | Raw | 1.94 ± 0.98 | 0.17 ± 0.53 |
| A5 | China | Vinegar-cooked | 3.36 ± 0.63 | 2.57 ± 0.20 |
| A6 | China | Vinegar-fried | 3.97 ± 0.10 | 2.78 ± 0.10 |

For analyzing syringin, Hypersil ODS (5 μm) 4.6 ID×250 mm column is used. A mobile phase is 28% methanol solution (mixed with water). A flow rate of the mobile phase is 1 mL/min. Absorbance of 270 nm is detected.

Referring to TABLE 1 and FIGS. 1A to 1F, group A3 shows a higher syringin content (3.46±0.21 mg/g) than groups A1 and A2. Group A6 also shows a higher syringin content (3.97±0.10 mg/g) than groups A4 and A5. That is, vinegar-frying apparently improves contents of syringin.

Furthermore, for analyzing elentheroside, Hypersil ODS (5 μm) 4.6 ID×250 mm column is used. A mobile phase is 14% acetonitrile solution (mixed with water). A flow rate of the mobile phase is 1 mL/min. Absorbance of 222 nm is detected.

Referring to TABLE 1 and FIGS. 2A to 2F, group A3 shows a higher elentheroside content (2.31±0.26 mg/g) than groups A1 and A2. Group A6 also shows a higher elentheroside content (2.78±0.10 mg/g) than groups A4 and A5. That is, vinegar-frying also apparently improves elentheroside content.

Trial (B): Active Ingredient Content of the *Zingiber officinale* Roscoe Extract Raw or fried samples shown in TABLE 2 are used in the trial (B). 1 gram of the sample is extracted via sonicated vibration for 2 hours by 20 mL of methanol. The resultant is filtrated by a No. 3 filter paper, followed by vacuum-concentration at 35° C. until the total volume is 5 mL.

TABLE 2

| Groups | Samples | | 6-Gingerol |
| | Origin | Processing | content (mg/g) |
| --- | --- | --- | --- |
| B1 | Taiwan | Raw | 37.46 ± 1.02 |
| B2 | Taiwan | Fried | 26.30 ± 0.97 |
| B3 | China | Raw | 28.04 ± 0.72 |
| B4 | China | Fried | 14.73 ± 0.90 |

For analyzing 6-gingerol, Hypersil ODS (5 μm) 4.6 ID×250 mm column is used. A mobile phase is 40% methanol solution (mixed with water). A flow rate of the mobile phase is 1 mL/min. Absorbance of 282 nm is detected.

Referring to TABLE 2 and FIGS. 3A to 3D, after frying, group B2 still contains 6-gingerol (26.30±0.97 mg/g). Group B4 also contains 6-gingerol (14.73±0.90 mg/g).

Trial (C). Toxicity

With reference to TABLE 3, the toxicity of the herbal extracts of groups C1 to C12 is tested in the trial (C). Group C0 without treatment is used as a control set.

TABLE 3

| Groups | Herbal extract | Origin | Processing |
| --- | --- | --- | --- |
| C1 | 8:1:1 | Taiwan | Raw[1] |
| C2 | 8:1:1 | Taiwan | Processed[2] |
| C3 | 7:2:1 | Taiwan | Raw[1] |
| C4 | 7:2:1 | Taiwan | Processed[2] |
| C5 | 6:3:1 | Taiwan | Raw[1] |
| C6 | 6:3:1 | Taiwan | Processed[2] |
| C7 | 8:1:1 | China | Raw[1] |
| C8 | 8:1:1 | China | Processed[2] |
| C9 | 7:2:1 | China | Raw[1] |
| C10 | 7:2:1 | China | Processed[2] |
| C11 | 6:3:1 | China | Raw[1] |
| C12 | 6:3:1 | China | Processed[2] |

[1]All of the *Acanthopanax senticosus* extract, the *Zingiber officinale Roscoe* extract and the *Coix lachryma-jobi L.* extract are extracted from the raw samples.
[2]The *Acanthopanax senticosus* extract, the *Zingiber officinale Roscoe* extract and the *Coix lachryma-jobi L.* extract are extracted from the vinegar-fried, fried and fried samples, respectively.

Undifferentiated 3T3-L1 cells are inoculated in DMEM medium containing 10% calf serum and 1% streptomycin-penicillin. The 3T3-L1 cells are cultured in an incubator with temperature of 37° C., $CO_2$ concentration of 5% and humidity of 95%. After 24 hours, 1 mL of the herbal extracts dissolving in RO water shown in TABLE 3 are added into the 3T3-L1 cells-cultured DMEM media, respectively. The 3T3-L1 cells are cultured in the incubator for further analysis.

Figure 5:
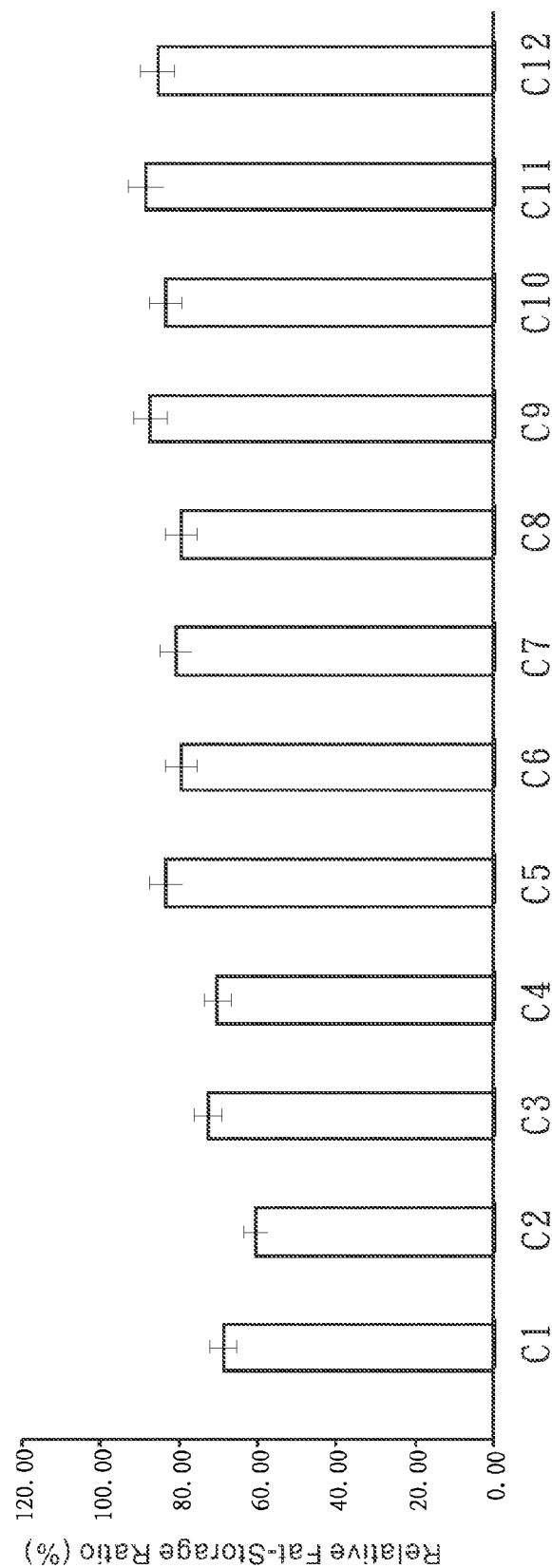
FIG. 5 depicts fat-storage ratio of groups C1 to C12.

After 24 hours, survival rates of the 3T3-L1 cells are analyzed by crystal violet staining assay. The 3T3-L1 cells are stained by crystal violet for 30 minutes, washed by water to remove excess crystal violet. Crystal violet will stain on the cell membrane of live cells. 2% SDS solution is used to dissolve crystal violet stained on the cell membrane. Finally, absorbance of 600 nm is measured. That is, the higher the survival rate is, the more crystal violet is dissolved, and therefore the higher the absorbance of 600 nm is measured. The relative fat-storage ratio shown in FIG. 5 is calculated as follows:

Relative survival rate (%)=(Survival rate of a testing set/survival rate of the control set)×100%

Figure 4:
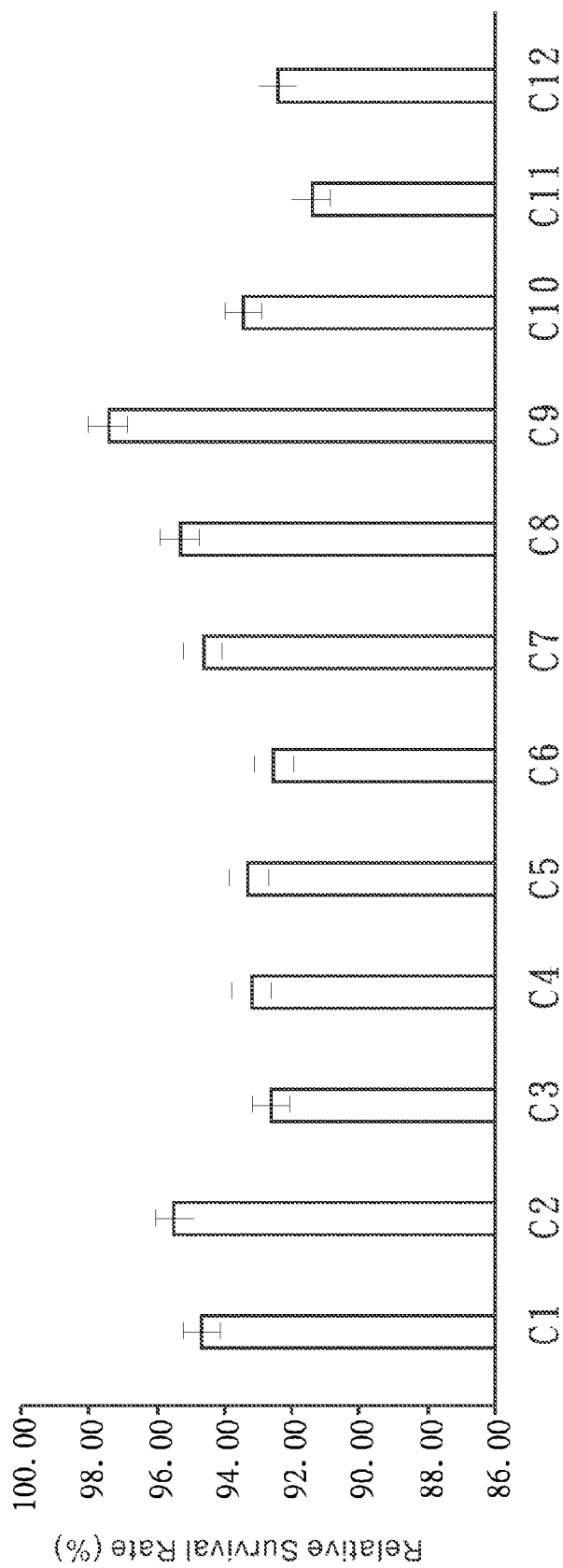
FIG. 4 depicts cell viability of adipocytes of groups C1 to C12.

Referring to FIG. 4, groups C1 to C12 show relative survival rate higher than 90%. That is, the herbal extract of the invention has no toxicity to 3T3-L1 cells, with no effect on inhibiting cell proliferation.

Trial (D): Anti-Fat Storage

DMEM medium formulas used in the trial (D) are shown in TABLE 4. The 3T3-L1 cells are resuspended in medium I and cultured in an incubator with temperature of 37° C., $CO_2$ concentration of 5% and humidity of 95% for 2 days. The 3T3-L1 cells are transferred to medium II and cultured for 3 days. The 3T3-L1 cells are then transferred to medium III for further culturing for 9 days. The 3T3-L1 cells are switched to fresh medium III every 2 days during the culturing of medium III. After 9 days, the 3T3-L1 cells become round with fat storing inside the cells. That is, undifferentiated 3T3-L1 cells are transformed to differentiated, mature adipocytes.

TABLE 4

| Formula | Contents | Concentration |
| --- | --- | --- |
| I | Dulbecco's modified Eagle's medium | |
| | Calf serum | 10% |
| | Streptomycin-penicillin | 1% |
| II | Dulbecco's modified Eagle's medium | |
| | Calf serum | 10% |
| | Streptomycin-penicillin | 1% |
| | Dexamethasone | 0.5 μM |
| | Isobutymethylxanthine | 0.5 mM |
| | Insulin | 10 μg/mL |
| III | Dulbecco's modified Eagle's medium, | |
| | Calf serum, | 10% |
| | Streptomycin-penicillin | 1% |
| | Insulin | 10 μg/mL |

Furthermore, the medium III-cultured 3T3-L1 cells are co-cultured with 1 mL of the herbal extract shown in the TABLE 3 for 9 days. Group C0 without treatment is used as a control set. After differentiation for 9 days, medium III is removed, and the 3T3-L1 cells are washed with phosphate buffer saline (PBS) twice. The 12-well plate stands at −80° C. for 1 hour, followed by standing at 37° C. for 20 minutes. 0.3 mL of deionized water is added to collect cell lysate, respectively. The collected cell lysates are sonicated vibrated at 4° C. for 30 minutes, and then kept in −20° C. for further analysis.

Triglyceride (TG) is a latter marker of adipocytes differentiation and TG/protein ratio is usually used to evaluate differentiation efficiency. The higher the TG/protein ratio is, the better the differentiation efficiency is. The relative fat-storage ratio shown in FIG. 5 is calculated as follows:

Relative fat-storage ratio (%)=(TG/protein ratio of a testing set/TG/protein ratio of the control set)×100%

The TG content is measured using a TG reagent (TR213, purchased from Randox Inc., Antrim, UK), and the protein content is measured following the Bradford method.

Referring to FIG. 5, groups C1 to C12 show reduced relative fat-storage ratio compared to group C0. Group C2 shows the lowest fat-storage ratio of 60%.

The herbal extract of the invention can inhibit fat-storage of adipocytes. Moreover, the herbal extract extracted from the processed samples shows preferable effect on inhibiting fat-storage function of adipocytes.

Trial (E): Animal Test

Specific pathogen free Wistar male rats (8 week-old, weight 200 to 250 grams) purchased from National Laboratory Animal Center, Taiwan are used in the trial (E). The rats are housed in an animal room with constant temperature of 25±1° C. where is kept on a 12-hours light and 12-hours dark cycle. The rats are housed and kept on free diet and water. After feeding with 60 kcal % fat diet (TestDiet® Formula 58Y1) for 4 weeks, rats with increased body weight over 40% are used as high-fat diet-induced obesity rat (HD rat) in the trial (E).

The herbal extract of the invention (group C2 shown in TABLE 3) is administered to the HD rats via gastrostomy in a dosage shown in TABLE 5. Group E0 with administration of RO water (1.5 mL/kg of body weight) is used as a control set. The herbal extract of the invention and RO water is administered to the HD rats once a day for 12 weeks.

TABLE 5

| | | Body weight (g) | | White fat tissue weight (mg/100 g body weight) | | | |
| --- | --- | --- | --- | --- | --- | --- | --- |
| Groups | Dosage (g/kg/day) | Week 0 | Week 12 | Beside epididymis | Kidney nearby | Mesentery | Groin |
| E0 | 0 | 215.7 ± 9.2 | 449.4 ± 8.3 | 440.7 ± 21.4 | 278.5 ± 18.3 | 208.5 ± 12.3 | 238.2 ± 10.7 |
| E1 | 0.1 | 214.2 ± 8.7 | 430.6 ± 7.2 | 424.5 ± 17.8 | 252.8 ± 17.9 | 189.6 ± 14.9 | 214.9 ± 12.3 |
| E2 | 0.3 | 216.2 ± 7.9 | 416.9 ± 8.1 | 377.9 ± 20.6* | 222.1 ± 20.4* | 174.6 ± 8.9* | 183.4 ± 10.9* |
| E3 | 0.6 | 213.9 ± 8.1 | 407.5 ± 6.4 | 315.8 ± 22.6* | 215.9 ± 18.4* | 162.1 ± 9.1* | 176.9 ± 11.2* |

*$P < 0.05$, compared with group E0

After 12 weeks, the HD rats are sacrificed, and white fat tissues beside epididymis, kidney, mesentery, and groin are weighed and recorded in TABLE 5.

Referring to TABLE 5, groups E1 to E3 show decreased body weight compared with group E0. Moreover, groups E2 and E3 show significantly decreased weight fat tissue beside epididymis, kidney, mesentery, and groin. That is, the herbal extract of the invention can effectively suppress fat-storage function of adipocytes, control increased body weights of the HD rats and keep the HD rats from overweight due to high-fat diet.

As a result, the herbal extract of the invention can effectively suppress differentiation of adipocytes, thereby preventing from fat-storage of adipocytes. Furthermore, by administrating the herbal extract of the invention, the subject in need can uptake active ingredients such as syringin, elentheroside and 6-gingerol, thereby preventing from obesity and obesity-derived diseases or conditions.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method of inhibiting fat-storage function of adipocytes comprising:
    administering an effective amount of an herbal extract to a target in need thereof,
    wherein the herbal extract consists of an *Acanthopanax senticosus* extract extracted from a vinegar-fried sample, a *Zingiber officinale* Roscoe extract extracted from a fried sample and a *Coix lachryma-jobi* L. extract extracted from a fried sample,
    wherein the weight percentage of the *Acanthopanax senticosus* extract is 60 to 80% by weight of the herbal extract, wherein the weight percentage of the *Zingiber officinale* Roscoe extract is 10 to 30% by weight of the herbal extract, wherein the weight percentage of the *Coix lachryma-jobi* L. extract is 10% by weight of the herbal extract.

2. The method of inhibiting fat-storage function of adipocytes as claimed in claim 1, wherein the weight percentage of the *Acanthopanax senticosus* extract is 80% by weight of the herbal extract, wherein the weight percentage of the *Zingiber officinale* Roscoe extract is 10% by weight of the herbal extract, wherein the weight percentage of the *Coix lachryma-jobi* L. extract is 10% by weight of the herbal extract.

3. The method of inhibiting fat-storage function of adipocytes as claimed in claim 1, wherein the herbal extract is orally administered to the target in need.

4. The method of inhibiting fat-storage function of adipocytes as claimed in claim 1, wherein the effect amount of the herbal extract is 100 to 600 mg/per kilogram of body weight per day.

5. The method of inhibiting fat-storage function of adipocytes as claimed in claim 4, wherein the herbal extract is administered for 12 weeks.

* * * * *